United States Patent [19]

Ferber et al.

[11] Patent Number: 4,643,571
[45] Date of Patent: Feb. 17, 1987

[54] CURRENT CONTROL SYSTEM FOR SPECTROPHOTOMETERS

[75] Inventors: Alan C. Ferber, Hillside; Morteza M. Chamran, deceased, late of Elmhurst, both of Ill., by Delories M. Chamran, legal representative

[73] Assignee: The Perkin-Elmer Corporation, Norwalk, Conn.

[21] Appl. No.: 651,191

[22] Filed: Sep. 14, 1984

[51] Int. Cl.[4] .................................................. G01J 3/10
[52] U.S. Cl. .................................... 356/326; 250/205; 250/461.1; 356/318
[58] Field of Search ............... 356/319, 323, 325, 326, 356/317, 318, 328; 250/205, 458, 459, 461.1, 461.2

[56] References Cited

U.S. PATENT DOCUMENTS

| 4,134,678 | 1/1979 | Brown et al. | 356/39 |
| 4,394,575 | 7/1983 | Nelson | 250/343 |
| 4,449,821 | 5/1984 | Lee | 356/319 |

Primary Examiner—F. L. Evans
Attorney, Agent, or Firm—E. T. Grimes; F. L. Masselle

[57] ABSTRACT

It has been shown that the use of a shutter to cut off the light beam entering the optical system of a fluoresence spectrophotometer will reduce UV deterioration of the components in the optical system. This invention discloses how control of the output of the light source by lowering its arc current when the shutter is closed can add significant improvement to the functioning of such a shutter system.

6 Claims, 2 Drawing Figures

CURRENT CONTROL SYSTEM FOR SPECTROPHOTOMETERS

FIELD OF INVENTION

This invention relates to spectrophotometers and, more particularly, to a current control system for a spectrophotometer source lamp.

RELATED PATENT APPLICATION

This application is related to U.S. patent application filed on even date herewith, Ser. No. 651,189, filed on Sept. 14, 1984, entitled "Automatic Shutter System", by Alan C. Ferber and Morteza M. Chamran, which is assigned to the same assignee. The subject matter contained therein is incorporated herein by reference.

BACKGROUND OF THE INVENTION

Generation of characteristic fluorescence in a sample solution undergoing analysis requires the solution to be irradiated with a high intensity light beam of selected wavelength, often in the ultraviolet range. The source for this beam is typically a monochromator using a high intensity source such as an Xenon arc. However, the high radiation level, which is necessary for the high measurement resolution desired, when it is in the near ultraviolet, below 300 nm, tends to deteriorate the optical elements in the pre-slit condensing system of the exciting monochromator. In a relatively short time, typically a few hundred hours, the reflectivity of the mirrors drops off drastically, especially in the ultraviolet, with the formation of scattering films on their surfaces where the optical beam strikes. Also, some types of optical filters, if used, tend to solarize or lose their optical UV transmission. These problems further extend to the collimating mirrors and the grating of the monochromator. In addition, heat build-up at the entrance slit and in the monochromator may cause wavelength shift and band-width errors.

The interposition of a shutter between the source and the optical system is an effective remedy for the deterioration problem discussed above. Such a shutter is the subject of a related U.S. patent application Ser. No. 651,189 previously identified. The use of such a shutter can also be extended to further improvement in the life of the source engendered by reduction of source current when the shutter is closed.

It is an objective of our invention to provide means for reducing the source current when the shutter closes without causing interference with the computer function or accuracy.

It is a further object of our invention to increase the source life by such a reduction of source current.

It is also an object of our invention to reduce the heat generated in the lamp and power supply when the shutter is closed.

It is in addition an object to lower the temperature of the shutter and shutter motor when the shutter is closed.

It is also an object to accomplish the above without inducing instability or drift of the source lamp's output.

BRIEF DESCRIPTION OF THE INVENTION

As indicated hereinbefore, it is advantageous in a high performance fluoresence spectrophotometer excited by a high intensity Xenon arc lamp source to incorporate a shutter which admits radiation from the source to the optical train of the instrument only when excitation is required as, for instance, when fluorescent measurements are being made. This condition is herein referred to as one of activity. While closing said shutter when no activity is present protects the optics from UV deterioration, certain problems also ensue. For instance, the radiation from the lamp heats the shutter to several hundred degrees centigrade when closed, resulting in the necessity of somehow removing about 150 watts of power without the shutter motor or other adjacent parts becoming excessively hot. Much of the energy reradiated as heat from the shutter may return to the Xenon source, aggravating its cooling requirements and possibly shortening lamp life.

To alleviate these cooling problems, according to the invention, means are provided by which the heat generated by the source may be substantially reduced whenever the shutter is closed. It is impractical to effect this reduction by extinguishing the source during shutter closure for at least three reasons, as follows: repeated firing and extinguishing of the source would shorten lamp life, especially because of ionic bombardment during the firing period; increased occurrence of starting transients would jeopardize digital operating routines; and further, lamp instability during the warm-up periods would deteriorate measurement accuracy and speed. We have found, however, that operation between a minimum and a maximum value of lamp current is possible without these difficulties. Selection of a suitable maximum operating current may be made whereby increased output and rapid stabilization occurs. Also a minimum standby current can be selected giving substantial reduction of generated heat, thus reducing temperature of the shutter and its motor. The maximum current, used on an intermittent basis does not shorten lamp life. Too low a standby current, however, surprisingly results in arc wander and destruction of internal lamp parts, thereby shortening lamp life. Hence, one aspect of our invention is directed to the proper selection and control of these current values, especially the standby current.

Control of source current is effected by a transistor control circuit in the lamp power supply. While the control signal to this circuit might be derived from the activity generated signal in the computer or the digital circuit which actuates the shutter, we have found this objectionable because of the large transients generated in the Xenon arc power supply. These transients are associated with the typically 7000 to 15000 volts, more or less, across the Xenon lamp during firing followed by around 12 volts during running. A direct cable connection to the digital system from the power supply is therefore undesirable. The invention, instead, derives the necessary control signal from a phototransistor, which monitors the presence or absence of the optical beam in the spectrophotometer and transfers the signal thus generated by means of an optoelectronic coupler, for voltage isolation, to the lamp control circuit. This isolates the lamp control circuit from the computer electronics in the spectrophotometer, resulting in photometric noise reduction and elimination of transient pickup.

The lamp power supply referred to in this disclosure is a regulated power supply, some of the basic principles and operation of which are the subject of U.S. Pat. No. 4,417,180, entitled "Lamp Firing Apparatus". The subject matter contained therein is incorporated herein by reference.

It will be apparent that a simple switch actuated by the shutter motion could presumably perform the same functions as the phototransistor control herein described. However, the power and torque requirements for the shutter motor would be much greater and reliability would be much less. The system cited in this invention disclosure, on the other hand, makes no demands whatever on the shutter or on the shutter power source.

There has thus been outlined rather broadly the more important features of the invention in order that the detailed description thereof that follows may be better understood, and in order that the present contribution to the art may better appreciated. There are, of course, additional features of the invention that will be described more fully hereinafter. Those skilled in the art will appreciate that the conception on which this disclosure is based may readily be utilized as the basis of the designing of other apparatus for carrying out the various purposes of the invention. It is important, therefore, that this disclosure be regarded as including such equivalent apparatus as do not depart from the spirit and scope of the invention.

One embodiment of the invention has been chosen for purposes of illustration and description and is shown in the accompanying drawings forming a part of the specification.

DETAILED DESCRIPTION OF A PRESENTLY PREFERRED EMBODIMENT

Figure 1:
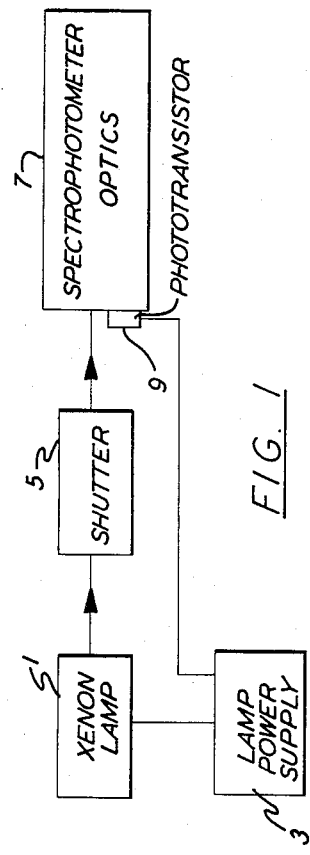
FIG. 1 is a block diagram showing the relationships and connections between components.

FIG. 1 is a simplified block diagram showing the components of the spectrophotometer of our invention and the interconnecting optical and electrical paths pertinent to the invention.

The Xenon lamp source 1 may be a VIX 150UV, 150 W Xenon Illuminator made by ILC Technology. This lamp source is powered by lamp power supply 3 whose function is twofold: to supply a maximum of 0.5 joules at 7 to 15 kV to start ionization in the lamp resulting in the firing of the lamp, and then to supply sustaining voltage to the arc. After firing, the voltage across the lamp drops to approximately 12 V at 12.5 A; to effect this the lamp must be temporarily supplied with 2 to 4 joules of energy at a voltage of 40 to 70 V. The circuits in the power supply provide, therefore, voltage and energy control during starting and subsequently regulate lamp current, as will be discussed hereinafter.

Mounted adjacent the output window of the lamp is a shutter 5 which opens to pass the light from the lamp when activity initiates a command from the computer as described in detail in the cited related application Ser. No. 651,189.

When the shutter is open the light beam enters the optical condenser system of the spectrophotometer 7. A small part of this light is intercepted by a phototransistor 9 which may be of any suitable type and mounted in the edge of the beam, preferably prior to the entrance slit of the excitation monochromator so as not to be a source of stray light scatter. This phototransistor when illuminated acts on the lamp power supply to increase the lamp current to its maximum normal operating value. On the other hand, when the shutter is closed this phototransistor is not illuminated and the lamp current is reduced.

Figure 2:
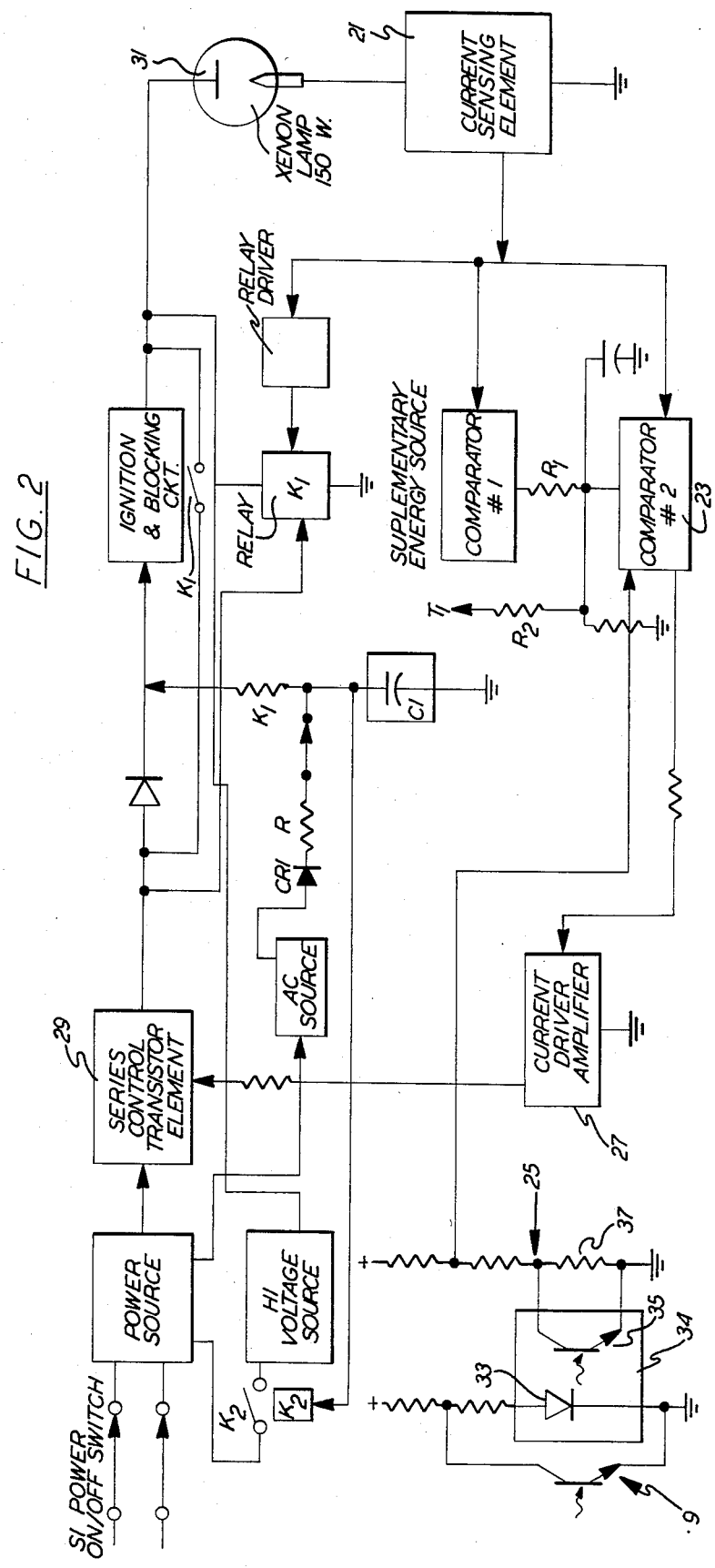
FIG. 2 is a simplified schematic of the lamp power supply showing the current control circuit.

To show how the lamp current is controlled by the above phototransistor, attention is directed to FIG. 2, which is a simplified schematic of the lamp power supply. Lamp current is monitored by a current sensing element 21, the measure of said current being applied as a voltage to a comparator network 23 where comparison is made with a regulated voltage from a divider indicated at 25. The output of the comparator 23, acting through a driver amplifier 27 adjusts the bias to a series control transistor element 29, which determines the current in the Xenon lamp 31. When the phototransistor 9 is darkened by the shutter closing, the phototransistor turns off and ceases to shunt LED 33 in the optoelectronic coupler module 34. When the LED lights up it turns on phototransistor 35. This phototransistor shunts resistor 37 in the divider 25 and causes the voltage to the comparator to change to a value which, through the control elements 27 and 29, reduces the lamp current to its standby value. When phototransistor 9 is illuminated by the shutter being open, the reverse of this control operation occurs, returning the lamp current to maximum operating value. Since the control process at all times is electronically independent of the computer digital circuit noise, transient pickup in the microprocessor system is minimized and higher performance sensitivity is possible.

The automatic switching from a high current when activity is present, shutter open, to low current on standby, shutter closed, affords heating reduction in the instrument and in the power supply. In our preferred embodiment the high current is set at 12.5 A, the low at 10 A, giving a reduction of about 30 percent in generated heat on standby. If necessary as much as a 2 to 1 power ratio may be used according to the manufacturer's claims for lamp life. However we have found that reduction to a standby current of 8 A (100 W) or less may cause the arc to wander, resulting in deterioration of the internal mirror of the lamp. The upper current limit is determined by the temperature of the ceramic/metal seals of the lamp. The practical limit is about 15 A (200 W). Within these limits our invention is effective in providing a significant reduction in instrument temperature, reducing measurement errors due to sample temperature drifts and increasing lamp life. Furthermore, within the current range utilized in the illustrated embodiment, we have found a prompt return of the lamp to its high light output level when the shutter opens, giving stable measurements.

Although a certain particular embodiment of the invention has been herein disclosed for purposes of explanation, various modifications thereof, after study of the specification, will be apparent to those skilled in the art to which the invention pertains.

What is claimed is:

1. A current control system for a spectrophotometer source lamp comprising, in combination:
    shutter means disposed between said source lamp and the entrance to the optical train of said spectrophotometer;
    phototransistor means disposed adjacent the entrance to said optical train for monitoring light from said source passed by said shutter means into said optical train;
    preset current regulated power supply means for establishing a first preselected current value to energize said source lamp when said shutter is open; and coacting power supply means driven by said phototransistor means to reduce the current to said source lamp to a second preselected value when said shutter is closed;

2. The system of claim 1 further comprising an excitation monochromator having an entrance slit and wherein said phototransistor means is mounted near the edge of the light beam prior to said light beam entering said entrance slit.

3. The system of claim 1 wherein said source lamp is a high intensity Xenon arc lamp.

4. The system of claim 1 wherein the value of current exciting said source lamp when said shutter is open is preselected for rapid statilization of said lamp.

5. The system of claim 1 wherein the value of current exciting said source lamp when said shutter is closed is preselected for minimized arc wander and long lamp life.

6. The system of claim 1 wherein said coacting power supply means includes optoelectronic coupling means.

* * * * *